(12) United States Patent
Wilkes et al.

(10) Patent No.: US 7,981,668 B2
(45) Date of Patent: Jul. 19, 2011

(54) SYSTEM AND METHOD FOR APPLYING REDUCED PRESSURE TO CELL CULTURE

(75) Inventors: Robert P. Wilkes, San Antonio, TX (US); Amy K. McNulty, San Antonio, TX (US); Kristine Kieswetter, San Antonio, TX (US); Teri D. Feeley, San Antonio, TX (US); Marisa Schmidt, San Antonio, TX (US)

(73) Assignee: KCI Licensing Inc., San Antonio, TX (US)

( * ) Notice: Subject to any disclaimer, the term of this patent is extended or adjusted under 35 U.S.C. 154(b) by 1117 days.

(21) Appl. No.: 11/624,017

(22) Filed: Jan. 17, 2007

(65) Prior Publication Data

US 2007/0166817 A1 Jul. 19, 2007

Related U.S. Application Data

(60) Provisional application No. 60/759,723, filed on Jan. 18, 2006.

(51) Int. Cl.
*C12M 3/00* (2006.01)

(52) U.S. Cl. ............... 435/305.3; 435/297.1; 435/297.2; 435/297.3; 435/297.5; 435/304.1; 435/304.2; 435/304.3; 435/305.1; 435/305.2; 435/305.4

(58) Field of Classification Search ............... 435/297.5, 435/297.1–297.3, 304.1–304.3, 305.1–305.4
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |

(Continued)

FOREIGN PATENT DOCUMENTS

AU 550575 A1 8/1982

(Continued)

OTHER PUBLICATIONS

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(Continued)

*Primary Examiner* — Michael A Marcheschi
*Assistant Examiner* — Jameson Q Ma

(57) ABSTRACT

A method and system for culturing cells, having a substantially airtight enclosure configured to culture cells. The method and system also have a first conduit configured to provide a reduced pressure to the substantially airtight enclosure and a second conduit configured to provide a culture media to the substantially airtight enclosure.

20 Claims, 14 Drawing Sheets

U.S. PATENT DOCUMENTS

| | | |
|---|---|---|
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,272,083 A * | 12/1993 | Butz et al. ............... 435/401 |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,474,065 A | 12/1995 | Meathrel et al. |
| 5,497,771 A | 3/1996 | Rosenheimer |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,665,596 A * | 9/1997 | Mussi ............... 435/373 |
| 6,071,267 A | 6/2000 | Zamierowski |
| 6,135,116 A | 10/2000 | Vogel et al. |
| 6,207,448 B1 | 3/2001 | Rozga et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0172412 A1 * | 8/2006 | Perrier et al. ............... 435/305.1 |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 02/072423 A1 | 9/2002 |
| WO | WO 02072423 A1 * | 9/2002 |

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

International Search Report and Written Opinion dated Oct. 24, 2008; International Application No. PCT/US07/01460.

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax,"*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

* cited by examiner

US 7,981,668 B2

SYSTEM AND METHOD FOR APPLYING REDUCED PRESSURE TO CELL CULTURE

CROSS-REFERENCES TO RELATED APPLICATIONS

This application claims priority to U.S. Provisional Patent Application No. 60/759,723, filed Jan. 18, 2006, the entire text of which disclosure is specifically incorporated by reference herein without disclaimer.

FIELD OF THE INVENTION

The present disclosure relates generally to methods and apparatus used to provide reduced pressure to cell cultures. More particularly, the present disclosure relates to methods and apparatus used to provide reduced pressure to cell cultures in a substantially airtight enclosure with controlled culture media flow.

BACKGROUND

Topical negative pressure (TNP) applications have been shown to be beneficial in the treatment of wounds by promoting granulation tissue formation, removing interstitial fluid, drawing wounds closed, and inducing microdeformations at the wound surface. In typical TNP applications, certain parameters may be varied, such as the pressure differential or fluid flow rates. However, it is not always possible to correlate variations in a particular parameter to a response in the wound therapy during in vivo applications, due to the lack of a controlled environment. It is therefore desirable to provide a method and apparatus for providing reduced pressure to cell cultures and measuring the effects of different parameters on TNP applications in a controlled in vitro environment.

It is also desirable to provide a method and apparatus for applying TNP that provides for controlled culture media flow rates and reduces the likelihood that air will be drawn into the cell culture. Such air induction can lead to desiccation of the matrix, thereby preventing meaningful data from being acquired.

SUMMARY OF THE INVENTION

In certain embodiments a cell culture system comprises a substantially airtight enclosure configured to culture cells; a first conduit in fluid communication with the substantially airtight enclosure, wherein the first conduit is configured to provide a reduced pressure to the substantially airtight enclosure; and a second conduit in fluid communication with the substantially airtight enclosure, wherein the second conduit is configured to provide a culture media to the substantially airtight enclosure. In other embodiments, a cell matrix is located within the substantially airtight enclosure, and the reduced pressure is applied to a first surface of the cell matrix and the culture media is applied to a second surface of the cell matrix during use. Other embodiments comprise a permeable surface and/or a dressing located within the substantially airtight enclosure. Still other embodiments comprise a permeable surface, a cell matrix and a dressing (or other manifolding material) located within the substantially airtight enclosure, wherein the culture media flows from the second conduit, through the permeable surface, through the cell matrix, through the dressing, and into the first conduit. In certain embodiments, the permeable surface supports the cell matrix and the cell matrix may be located between the permeable surface and the dressing.

Other embodiments comprise a sealing system for a cell culture system comprising a peripheral sealing member configured to engage a plate well and configured to engage a cell culture insert, such that a first seal is formed between the peripheral sealing member and the plate well and a second seal is formed between the peripheral sealing member and the cell culture insert. An insert sealing assembly may also be configured to engage the cell culture insert such that a third seal is formed between the insert sealing assembly and the cell culture insert. In certain embodiments, the peripheral sealing member may be configured to engage an interior wall of the plate well and an exterior wall of the cell culture insert and the insert sealing assembly may be configured to engage an interior wall of the insert. In certain embodiments, a first conduit may extend through the peripheral sealing member and a culture media supply system may be coupled to the first conduit. In other embodiments, second conduit may extend through the peripheral sealing member and a third conduit may extend through the insert sealing assembly. In certain embodiments a low pressure source may be coupled to the third conduit and a fourth conduit may extend through the insert sealing assembly. In certain embodiments the first and second seals may each be created by an interference fit and the peripheral sealing member may be formed by injection molding. In certain embodiments, the insert sealing assembly may comprise an insert sealing member, an insert seal ring, a lateral sealing member, and an insert manifold. In certain embodiments, the insert sealing member and/or the insert manifold may be pressed into the insert. In other embodiments, the insert manifold is threaded into the insert sealing member. In certain embodiments, the insert seal ring may be compressed between the insert sealing member and the insert manifold and the insert sealing member may be formed by injection molding. In certain embodiments, the peripheral sealing member is pressed into the plate well.

Other embodiments comprise a method of culturing cells comprising: providing a substantially airtight enclosure; providing a cell matrix within the substantially airtight enclosure; providing a reduced pressure to the substantially airtight enclosure; and providing a culture media to the substantially airtight enclosure. In certain embodiments, the substantially airtight enclosure comprises a first surface and a second surface, and the reduced pressure is applied to the first surface and the culture media is applied to the second surface. In certain embodiments, the reduced pressure is provided via a first conduit coupled to a low pressure source and the first conduit is in fluid communication with the substantially airtight enclosure. In certain embodiments, the low pressure source is a vacuum pump. In certain embodiments, the culture media may be provided via a second conduit coupled to a culture media supply system and the second conduit is in fluid communication with the substantially airtight enclosure.

Other embodiments comprise a system for culturing cells comprising: a plate well; a cell culture insert; a peripheral sealing member configured to engage a plate well and configured to engage the cell culture insert, such that peripheral sealing member forms a first seal with the plate well and forms a second seal with the cell culture insert; and an insert sealing assembly configured to engage the cell culture insert such that the insert sealing assembly forms a third seal with the cell culture insert. Certain embodiments comprise a first conduit extending through the peripheral sealing member and a low pressure source coupled to the first conduit. In certain embodiments, the second conduit may extend through the insert sealing assembly and a culture media supply system may be coupled to the second conduit. Certain embodiments also comprise a cell matrix in the cell culture insert and a dressing between the cell matrix and the insert sealing assembly.

DETAILED DESCRIPTION OF DISCLOSED EMBODIMENTS

Figure 1:
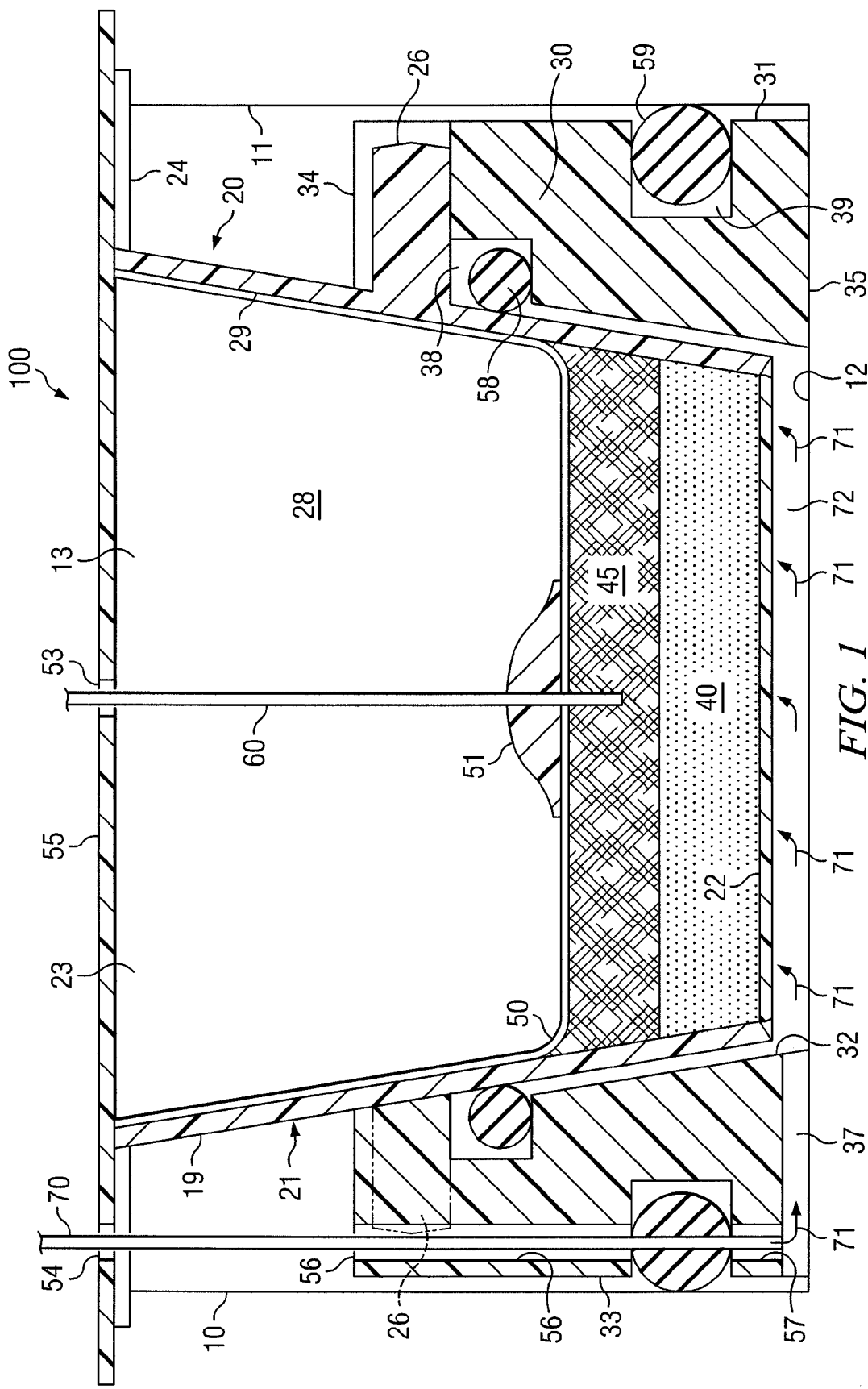
FIG. 1 illustrates a cross-sectional view of a first embodiment of a cell culture system.
Figure 2:
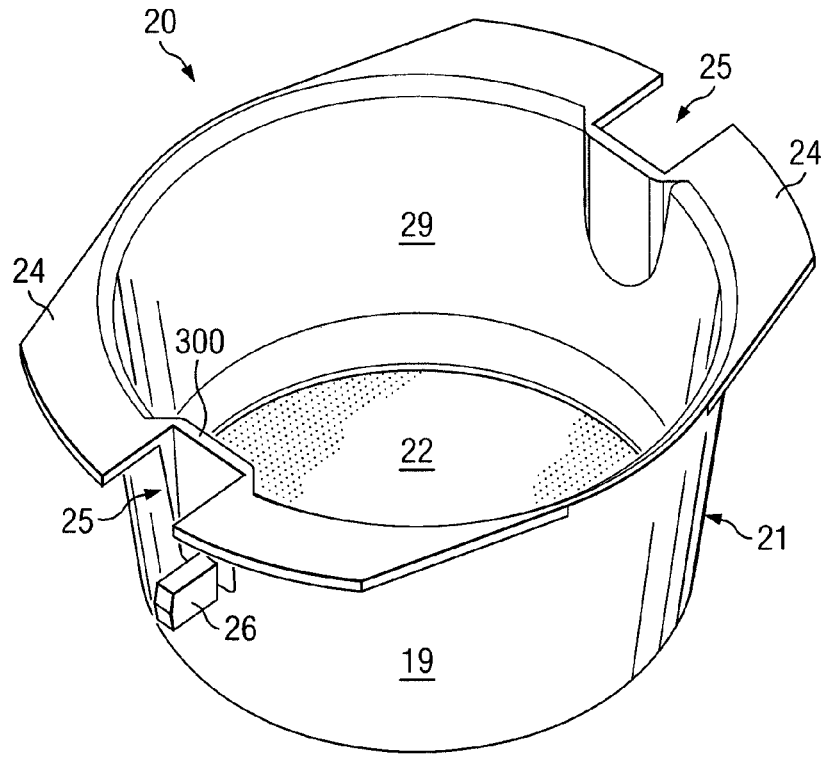
FIG. 2 illustrates a perspective view of a cell culture insert.

Referring initially to FIGS. 1 through 4, a cell culture system 100 comprises a plate well 10, a cell culture container 20 for growing cell cultures, and a peripheral sealing member 30 between plate well 10 and cell culture container 20. In this embodiment, plate well 10 comprises a peripheral interior wall 11 between a base 12 and an open end 13. In the embodiment shown, cell culture container 20 comprises a tapered body 21 with an exterior wall 19 and an interior volume 28 bounded by a permeable membrane 22 at one end, an open end 23 that is opposite permeable membrane 22, and an inner perimeter 29. In this embodiment, open end 23 comprises a flange 24 with a pair of notches 25, and a pair of tabs 26 extend from tapered body 21 in axial alignment with notches 25. During use, the disclosed embodiment also comprises a cell matrix 40 between permeable membrane 22 and a dressing 45. In certain embodiments, cell matrix 40 encapsulates multiple layers of cells. In addition, a lid 55 comprising holes 53 and 54 may be used to secure cell culture container 20 in plate well 10 during use. In certain embodiments, cell culture container 20 may be a BD Falcon™ 6-well insert, plate well 10 may be a BD Falcon™ 6-well culture plate, and dressing 45 may be an open-cell foam or a gauze.

Figure 3:
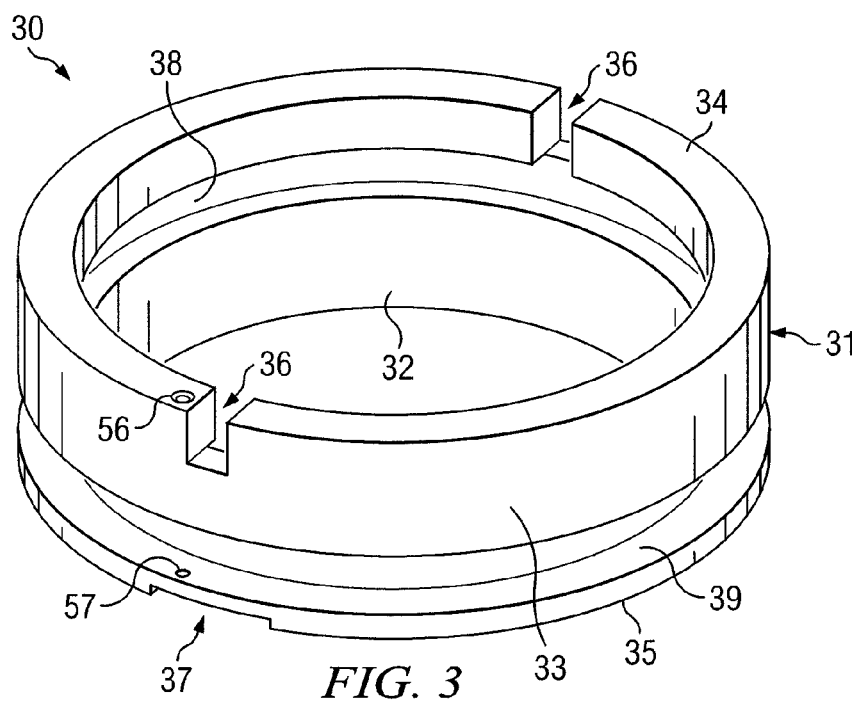
FIG. 3 illustrates a perspective view of one embodiment of a peripheral sealing member.
Figure 4:
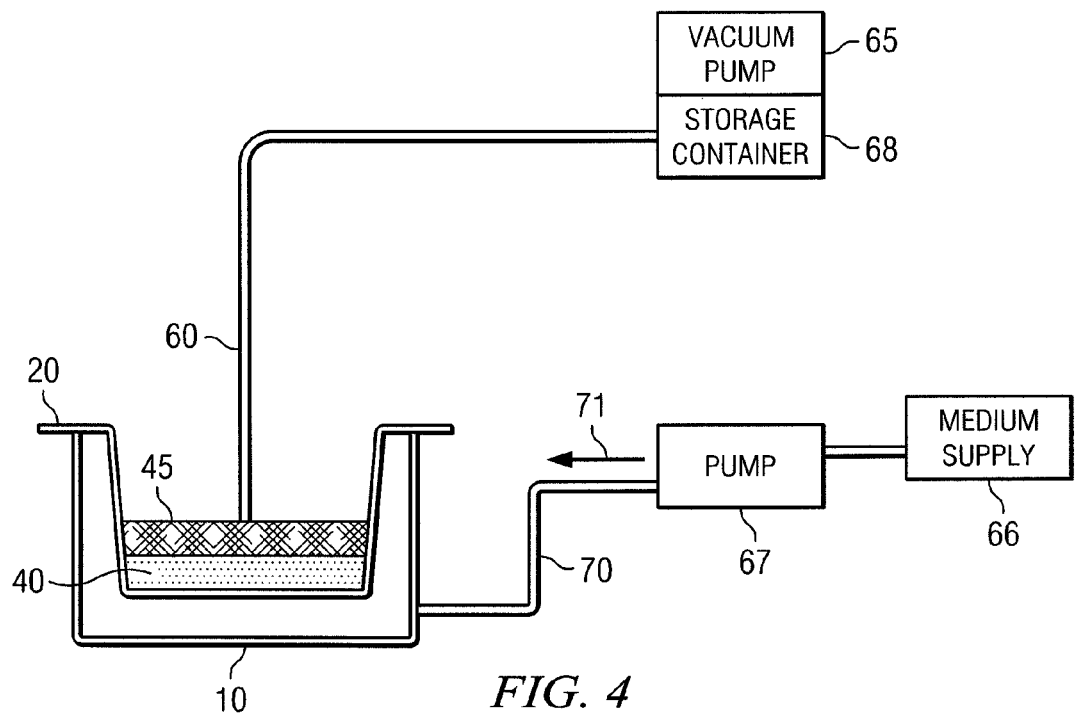
FIG. 4 illustrates a schematic view of one embodiment of a cell culture system.

In the embodiment of FIG. 3, peripheral sealing member 30 comprises a body 31 that is substantially cylindrical and comprises an interior surface 32, an exterior surface 33, a notched end 34 and a channeled end 35. In this embodiment, notched end 34 comprises a pair of notches 36 configured to align with tabs 26 of cell culture container 20. In the disclosed embodiment, a channel 37 extends across channeled end 35 from exterior surface 33 to interior surface 32. As shown, exterior surface 33 comprises a relief 39 and interior surface comprises a relief 38. In this embodiment, relief 38 is configured to receive a flexible sealing member 58 and relief 39 is configured to receive a flexible sealing member 59. In certain embodiments, flexible sealing members 58 and 59 may be o-rings. In other embodiments, flexible sealing members may be gaskets, v-rings, or other suitable devices. In this embodiment, peripheral sealing member 30 also comprises a cavity 56 that extends through body 31 from notched end 34 to relief 39 and a cavity 57 that extends from relief 39 to channel 37.

During use, the embodiment of FIGS. 1 through 4 also comprises a lateral sealing member or drape 50 (with a reinforcing member 51) that extends across inner perimeter 29. In this embodiment, a suction conduit 60 extends through hole 53, reinforcing member 51, drape 50 and into dressing 45 during operation. Suction conduit 60 is therefore in fluid communication with components on each side of drape 50.

In addition, a culture media conduit 70 provides culture media to cell matrix 40 during use of this embodiment. In the embodiment shown, culture media conduit 70 extends through hole 54, notch 25, cavity 56, relief 39, flexible sealing member 59, and into cavity 57. Cell culture media conduit 70 is therefore in fluid communication with components on each side of peripheral sealing member 30. As shown in the schematic in FIG. 4, suction conduit 60 may be coupled to a low pressure source 65 and culture media conduit 70 may be coupled to a media supply system 66 comprising a pump 67. In certain embodiments, pump 67 may comprise a peristaltic pump and low pressure source 65 may comprise a vacuum pump. In the embodiment shown in FIG. 4, material (such as air and fluid) drawn through suction conduit 60 may be stored in a storage container 68.

Figure 6:
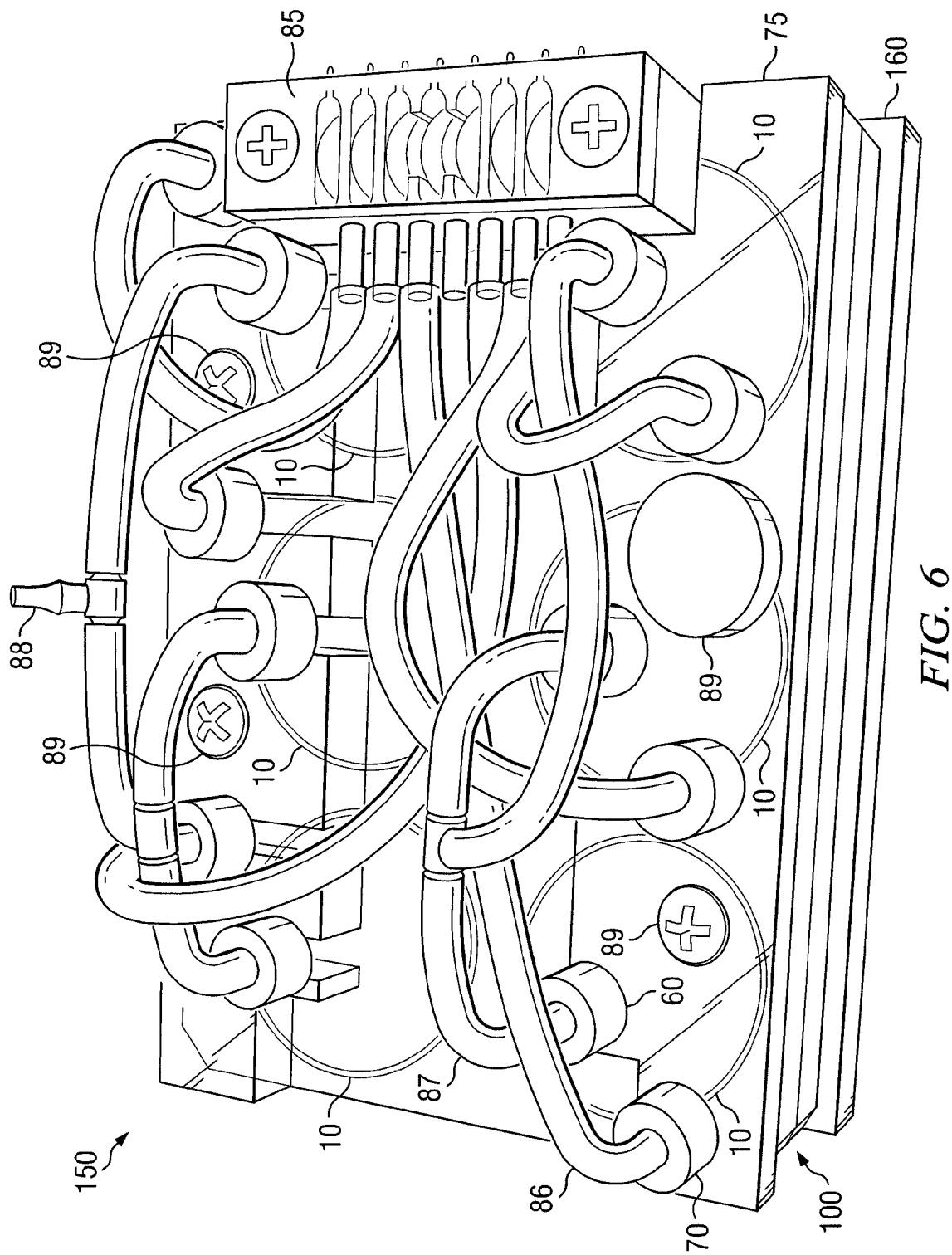
FIG. 6 illustrates a perspective view of one embodiment of a cell culture system incorporating the embodiment of FIG. 1.

During use, cell culture system 100 provides topical negative pressure (TNP) to cell matrix 40 and provides culture media 71 to cell matrix 40. In one embodiment, peripheral sealing member 30 (with flexible sealing members 58 and 59) is placed in plate well 10 so that flexible sealing member 59 engages plate well 10. In this embodiment, cell culture container 20 (comprising cell matrix 40) is placed in peripheral sealing member 30 so that flexible sealing member 58 engages cell culture container 20 and tabs 26 align with notches 36. In certain embodiments, dressing 45 is placed on cell matrix 40 and drape 50 is placed across open end 23 of cell culture container 20. As shown in FIG. 6 and discussed more fully below, lid 55 may be assembled with suction conduit 60 and reinforcing member 51 to form a lid assembly 75. Lid assembly 75 may be positioned to cover drape 50, plate well 10, and open end 23 of cell culture container 20. In certain embodiments, as lid assembly 75 is lowered into place, suction conduit 60 penetrates drape 50 and reinforcing member 51 pushes down on drape 50. In certain embodiments, drape 50 is a polyurethane sheet, approximately 0.002-0.004 inches thick, with an adhesive on the side proximal dressing 45. As assembled, suction conduit 60 extends into dressing 45. Culture media conduit 70 may be inserted through hole 54, notch 25, cavity 56, relief 38, flexible sealing member 58, and into cavity 57 or channel 37 (which is in fluid communication with cavity 56).

As shown in FIG. 1, cell culture system 100 is configured to provide topical negative pressure (TNP) and culture media 71 to cell matrix 40. In the embodiment shown, media supply system 66 can supply culture media 71 to culture media conduit 70 during use. Culture media 71 can exit conduit 70 and travel through channel 37 toward cell culture container 20. In this embodiment, culture media 71 then travels through a gap 72 between permeable membrane 22 and base 12. As shown, culture media 71 passes then passes through permeable membrane 22 to cell matrix 40, thereby providing nutrients for cell matrix 40 to culture cells during use.

In addition, cell culture system 100 also may provide topical negative pressure (TNP) to cell matrix 40. During operation, low pressure source 65 can create a negative or suction pressure through suction conduit 60 and into dressing 45. Because dressing 45 is a porous material (such as open-cell foam or cotton gauze), cell matrix 40 is also exposed to the suction pressure. Cell matrix 40 is therefore exposed to a pressure differential that encourages the top portion of cell matrix 40 to conform to the bottom surface of dressing 45, which may have an irregular surface comprising indentations and raised portions. Such a process of deforming the cell matrix 40 by contact with a non-planar surface (known as microdeformation) can stimulate cellular activity in the cell matrix through the induction of mechanical strain (known as mechanotransduction). In addition, the pressure differential across cell matrix 40 also promotes the migration of culture media 71 into cell matrix 40, further promoting growth of cells in cell matrix 40. Furthermore, the pressure differential across drape 50 can cause drape 50 to deform to cell culture container 20 and dressing 45.

As shown in FIG. 1, cell culture system 100 incorporates features that provide for the effective application of TNP to cell matrix 40. For example, flexible sealing members 58 and 59 restrict the amount of air that may be drawn from between cell culture container 20 and plate well 10 and into suction conduit 60. In addition, drape 50 forms a seal along the interior wall of cell culture container 20 and across dressing 45, further restricting air flow into suction conduit 60. Furthermore, the flow rate of culture media 71 may be controlled by adjusting the pressure differential created across permeable membrane 22, cell matrix 40, and dressing 45. By controlling parameters such as the amount of air flow through suction conduit 60 and the pressure drop across cell matrix 40, the likelihood that cells from cell matrix 40 will enter suction conduit 60 and be removed from cell culture container 20 is reduced. Cell culture system 100 thereby provides an effective method of applying TNP to cell matrix 40 while minimizing the risk that cells will be lost.

Figure 5:
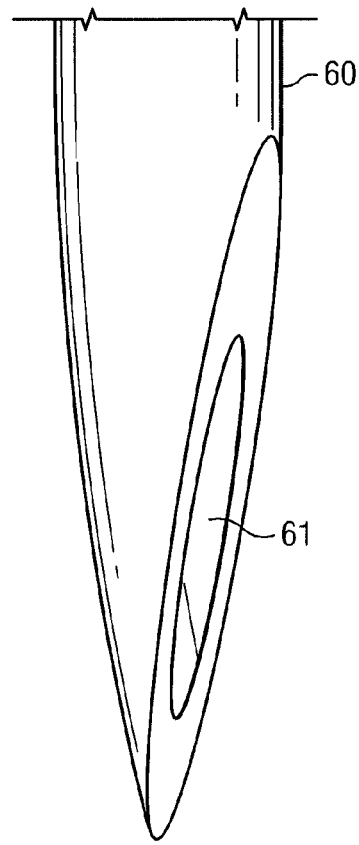
FIG. 5 illustrates a detailed view of one embodiment of a conduit.

In the embodiment disclosed in FIGS. 1 through 4, suction conduit 60 comprises a 25-GA hypodermic needle with a deflected non-coring tip 61, as shown in FIG. 5. Non-coring tip 61 can reduce the likelihood that material will clog the tip as it is penetrating a surface such as flexible sealing member 58 or reinforcing member 51. In certain embodiments, culture media conduit 70 may also comprise a 25-GA hypodermic needle with a deflected non-coring tip. In the disclosed embodiments, reinforcing member 51 comprises a rubber dome-shaped device with an adhesive flat side. In certain embodiments, reinforcing member 51 is a product sold by 3M under the Bumpon™ trademark. Disclosed embodiments also comprise flexible sealing members 58 and 59 having a durometer of approximately 70. Other embodiments may comprise individual features with different specifications from those provided above, which are provided for example purposes only.

In certain embodiments, cell culture system 100 may be part of a larger assembly. As shown in FIG. 6, cell culture assembly 150 comprises a six well plate 160 with six individual plate wells 10. Each cell culture system 100 comprises a culture media conduit 70 near the perimeter of plate well 10 and a suction conduit 60 near the center of plate well 10. For purposes of clarification, only one cell culture system 100 is labeled in FIG. 6. In the embodiment shown, each culture media conduit 70 is coupled to a bulkhead 85 via flexible tubing 86. Bulkhead 85 may then be coupled to multiple media supply systems 66 (shown in FIG. 4). In this embodiment, control parameters, such as flow rate or media type, can be controlled individually for each cell culture system.

In addition, each suction conduit 60 is coupled together via flexible tubing 87 to a common connector 88. Common connector 88 may then be coupled to a low pressure source such as vacuum pump 65 (shown in FIG. 4). In other embodiments, each suction conduit 60 may be individually coupled to separate low pressure sources, so that the pressure may be individually controlled for each cell culture system 100. Also visible in the embodiment shown in FIG. 6 are fasteners 89 used to secure lid assembly 75 to six well plate 160. In certain embodiments, components of cell culture assembly 150 (such as lid assembly 75 and well plate 160) are comprised of material that allows light to pass through them. In such embodiments, cell matrix 40 can be observed during the cell culture process for evaluation purposes (including, for example, fluorescent responses to stimuli).

In certain embodiments, cell matrix 40 is porous enough to allow media culture 71 to flow through it, and strong enough to withstand TNP without cell proliferation. One example of such a matrix comprises porcine whole blood in sodium citrate spun down to separate out the cells from the plasma. In this embodiment, plasma may be assayed for fibrinogen and 2 mL of 9.8 mg/mL is placed in each cell culture container 20. The cells may then be seeded into plasma at approximately 20,000 cells per cell culture container 20, and 0.5 mL of Thrombin (1083 units per mL in culture media 71) may be added drop-wise onto the plasma/cell mixture. After cell matrix 140 has set up, culture media 71 can be added to the bottom of cell culture container 20 and to the top of cell matrix 140. In this embodiment, cells may be allowed to proliferate for approximately two weeks prior to further experimentation. In certain embodiments, immediately prior to experimentation, 1 mL of an agar (such as Tryptic Soy agar at a concentration of 40 g/L) may be added to the top of the matrix. The thin agar layer can be used to stabilize cell matrix 140 during TNP while still being porous enough to allow fluid flow.

Figure 7:
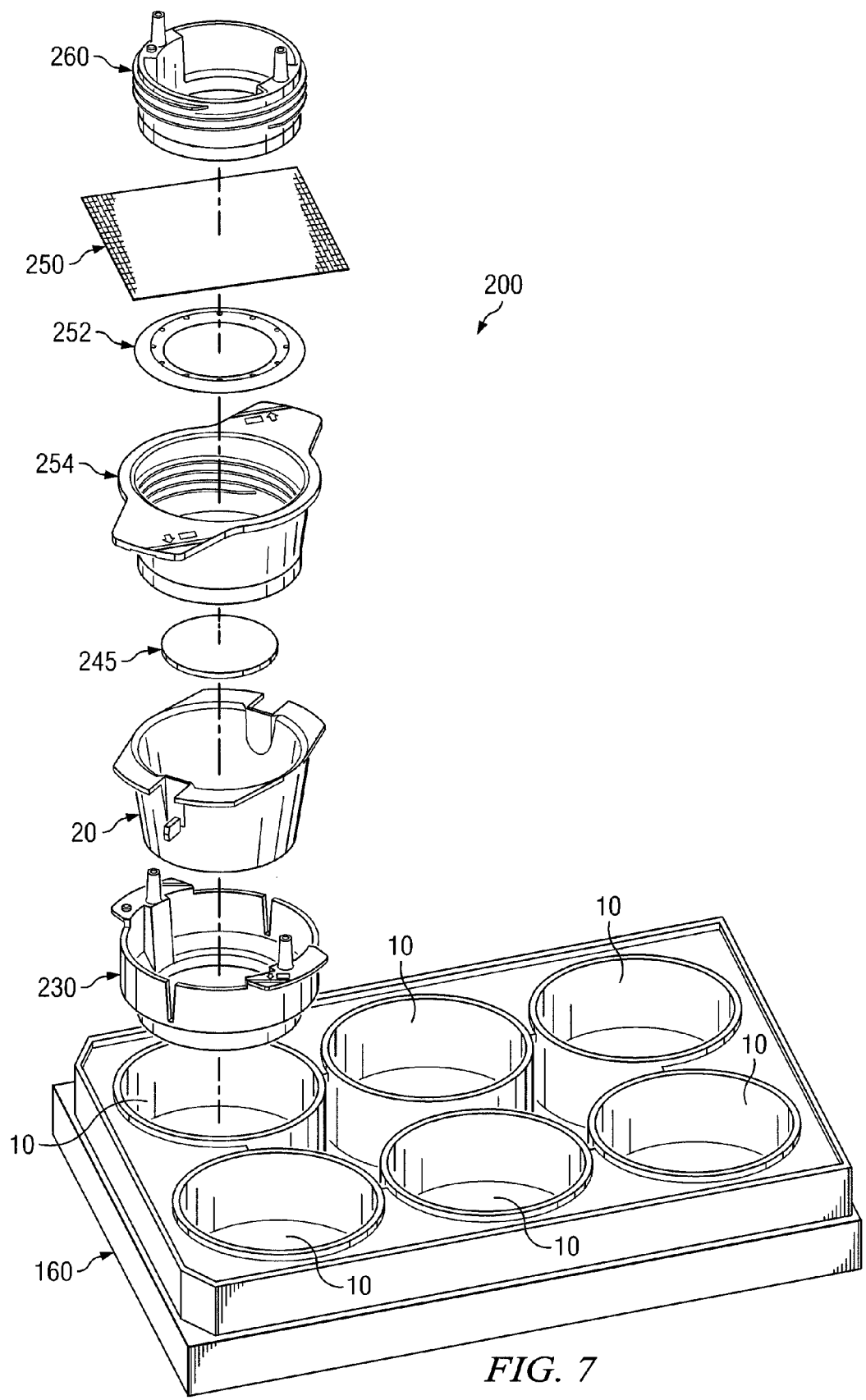
FIG. 7 illustrates an exploded view of one embodiment of a cell culture system.

Another embodiment of a cell culture system 200 is shown in FIGS. 7-22. In the exploded view of FIG. 7, cell culture system 200 comprises plate well 10 in six well plate 160. In the embodiment shown, inserted into plate well 10 are a peripheral sealing member 230, cell culture container 20, a dressing 245, an insert sealing member 254, an insert seal ring 252, a lateral sealing member or drape 250, and an insert manifold 260. Referring now to the assembled cross-section view of FIG. 8, peripheral sealing member 230 has been radially oriented and pressed into plate well 10 and cell culture container 20 has been radially oriented and pressed into peripheral sealing member 230 in this embodiment. During use, cell matrix 240 is placed on top of permeable membrane 22. Dressing 245 may then be placed on top of cell matrix 240 and insert sealing member 254 can be radially oriented and pressed into cell culture container 20. In the embodiment shown, drape 250 can then be placed onto insert seal ring 252, which can then be placed onto a lip 253 of insert sealing member 254. Insert manifold 260 can be threaded into insert sealing member 254.

Figure 9:
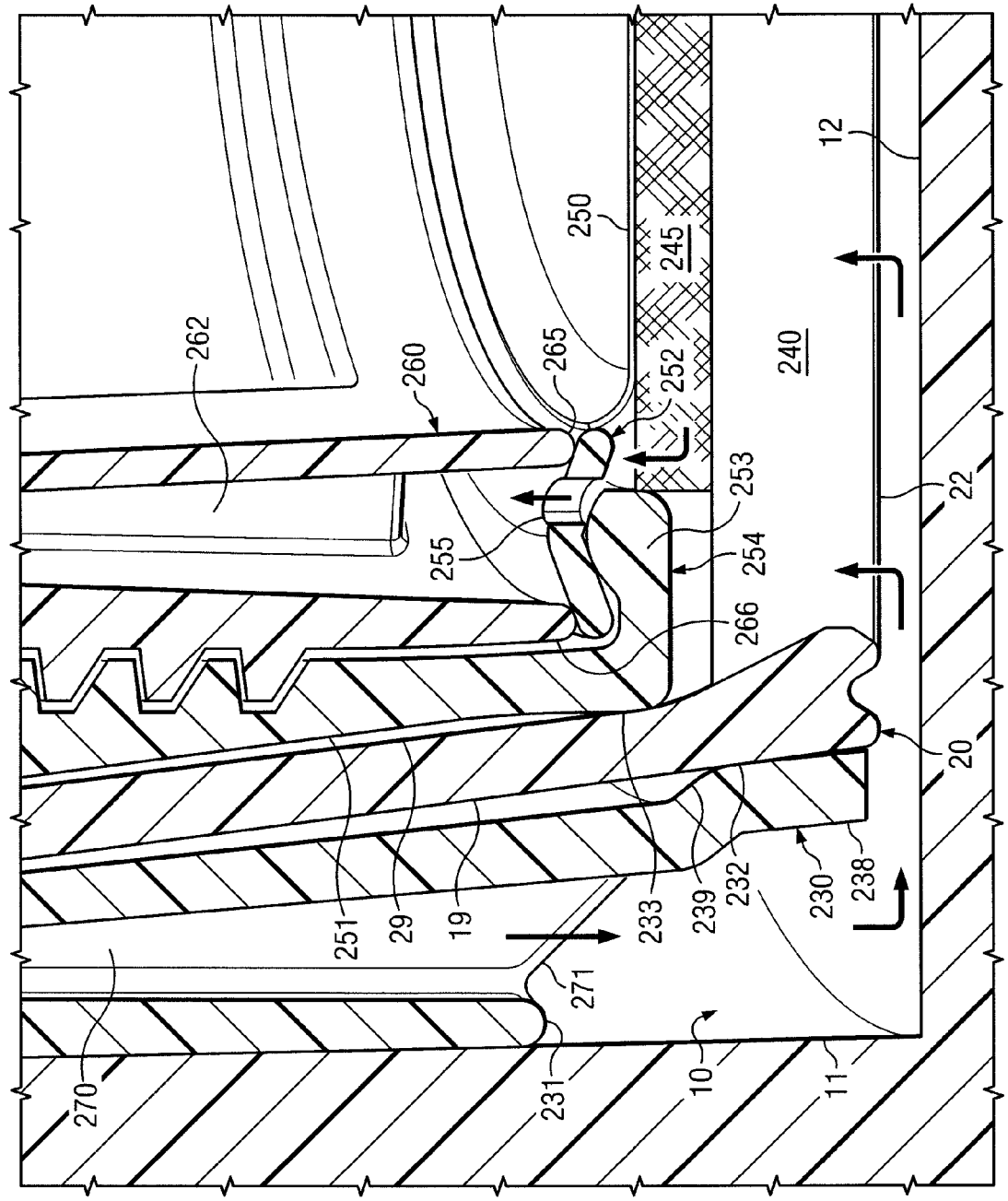
FIG. 9 illustrates a detailed cross-sectional view of the embodiment of FIG. 7.

Referring now to the detailed cross-section of FIG. 9, a body 231 of peripheral sealing member 230 engages interior wall 11 of plate well 10 to create a substantially air-tight seal (via an interference fit) between plate well 10 and peripheral sealing member 230. While peripheral sealing member 230 directly contacts plate well 10 in this embodiment, other embodiments may comprise additional components between peripheral sealing member 230 and plate well 10. In this embodiment, multiple seals are formed via interference fits; in other embodiments, substantially air-tight seals can be formed through other mechanisms such as o-rings, gaskets, sealants, etc. Additional substantially air-tight seals are formed where peripheral sealing member 230 engages cell culture container 20 in region 232 and where cell culture container 20 contacts insert sealing member 254 at region 233. In the embodiment shown, drape 250 is placed on insert seal ring 252, which is placed on lip 253 of insert sealing member 254. In this embodiment, insert seal ring 252 comprises one or more apertures 255, and drape 250 can be punctured to create apertures (not shown) that align with apertures 255, allowing the space directly above apertures 255 to be in fluid communication with the space below apertures 255. Insert manifold 260 can then be threaded into insert sealing member 254, thereby securing drape 250 against insert seal ring 252, and insert seal ring 252 against lip 253.

Figure 8:
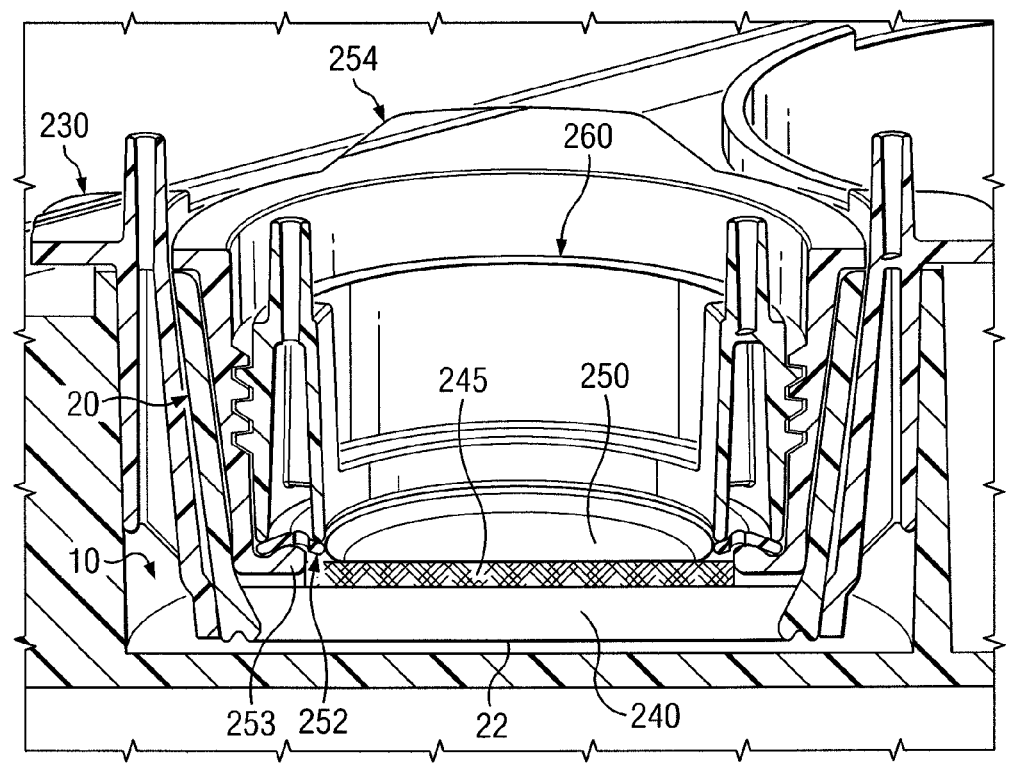
FIG. 8 illustrates a cross-sectional view of the embodiment of FIG. 7.

As shown in FIGS. 8 and 9, a conduit 270 extends through peripheral sealing member 230, providing a path for culture media 271 to reach cell matrix 240 through permeable membrane 22 (similar to the manner described in the previous embodiment). Also shown in this embodiment, insert manifold 260 comprises a conduit 262 in fluid communication with apertures 255 of insert seal ring 252 and any apertures provided in drape 250. Therefore, a low pressure source (such as vacuum pump 65 in FIG. 4) may be coupled to conduit 262 and provide low pressure or suction to dressing 245 to cause microdeformation and mechanotransduction of cell matrix 240 in a manner similar to the previously-described embodiment.

Figure 10:
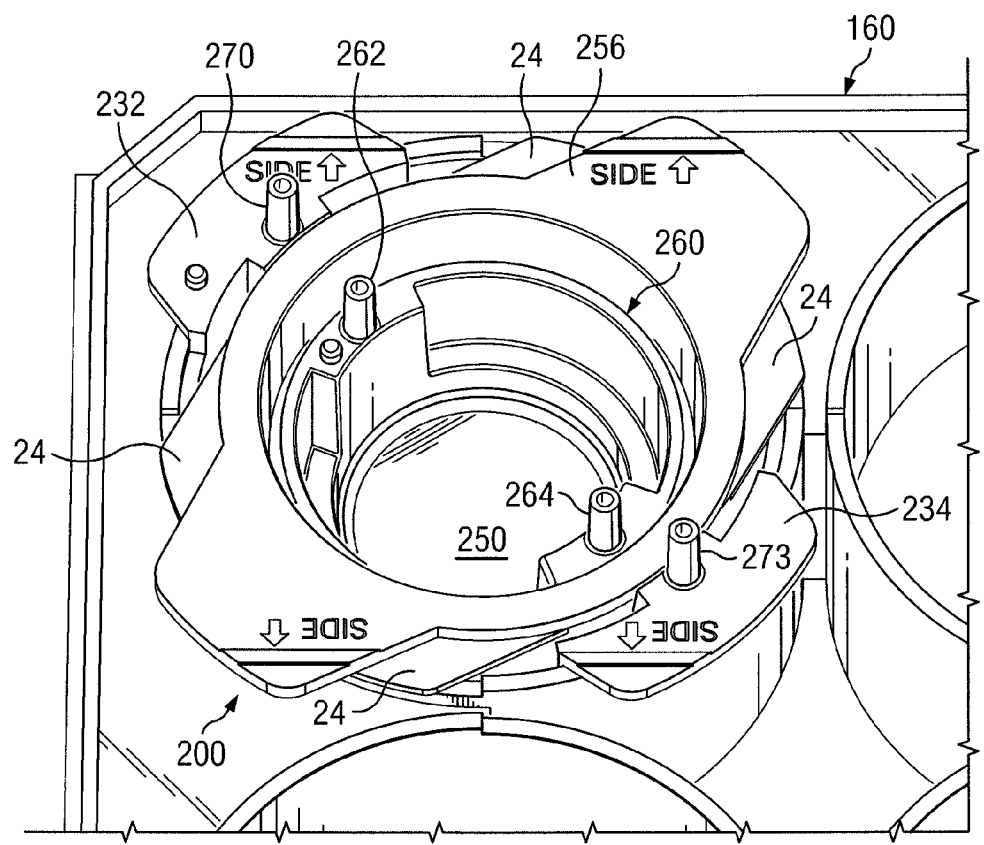
FIG. 10 illustrates a top perspective view of the embodiment of FIG. 7.

A top view of assembled cell culture system 200 is shown in FIG. 10. Shown extending from plate well 10 in this embodiment, peripheral sealing member 230 comprises tabs 232 and 234, cell culture container 20 comprises flanges 24, and insert sealing member 254 comprises tabs 256. In this embodiment, tabs 232, 234, and 256 comprise indicia regarding alignment of the components, as well as indicia to denote whether a port is open (discussed in more detail below).

Figure 11:
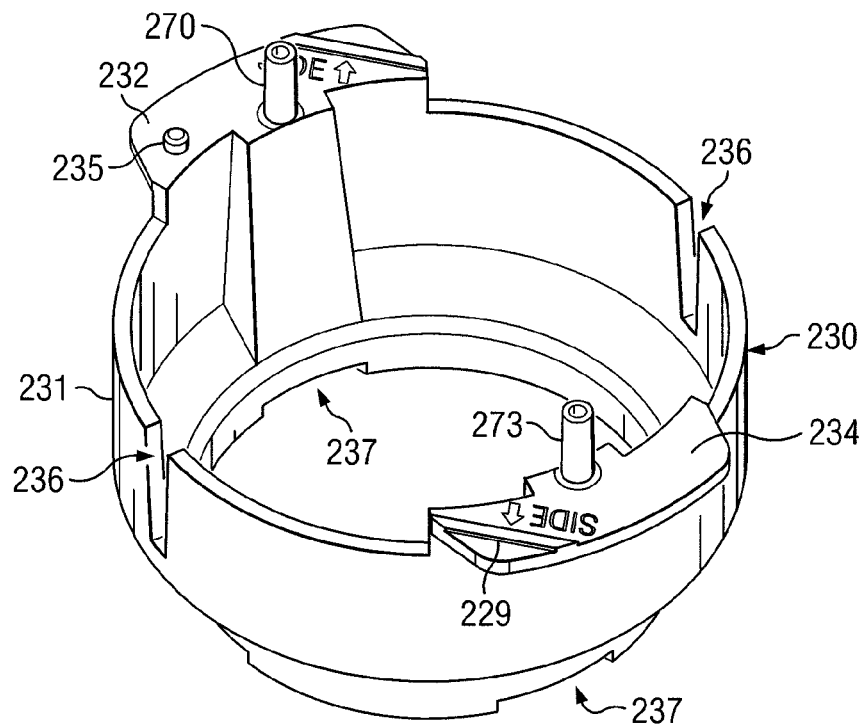
FIG. 11 illustrates a top perspective view of one embodiment of a peripheral sealing member.
Figure 12:
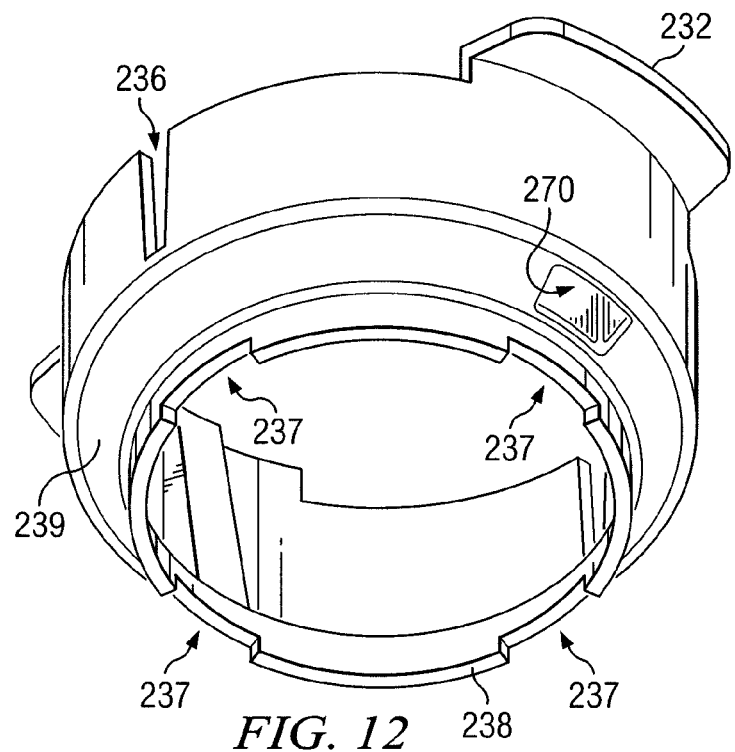
FIG. 12 illustrates a bottom perspective view of the embodiment of FIG. 11.
Figure 13:
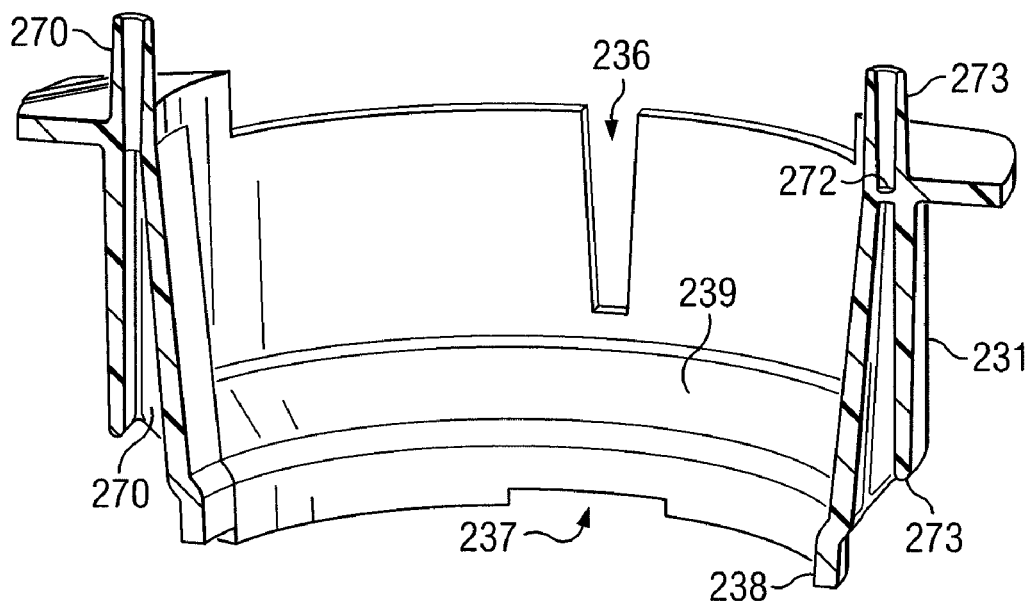
FIG. 13 illustrates a cross-sectional view of the embodiment of FIG. 11.

Referring now to FIGS. 11-13, more detailed features of peripheral sealing member 230 are visible. In this embodiment, peripheral sealing member 230 comprises a body 231 that is substantially cylindrical with a pair of notches 236, tabs 232 and 234, conduit 270 and a sealed conduit 273. Notches 236 are configured to align with tabs 26 extending from cell culture container 20 (shown in FIG. 2). Sealed conduit 273 comprises a septum 272 that can be punctured if it is desired to open sealed conduit 273 so that it may be used for a secondary pathway for culture media 271 or a pressure sensing port. A bump 235 on tab 232 indicates that conduit 270 extending from tab 232 is open rather than sealed and indicia 229 provide guidance for alignment during assembly. At the end of body 231 opposite of tabs 232 and 234 is a tapered portion 239 extending to a collar 238 with channels 237. Similar to channels 37 of the previously-described embodiment, channels 237 provide a pathway for culture media 271 to flow from conduit 270 to permeable membrane 22 and cell matrix 240, thereby providing nutrients for cell matrix 240.

Figure 14:
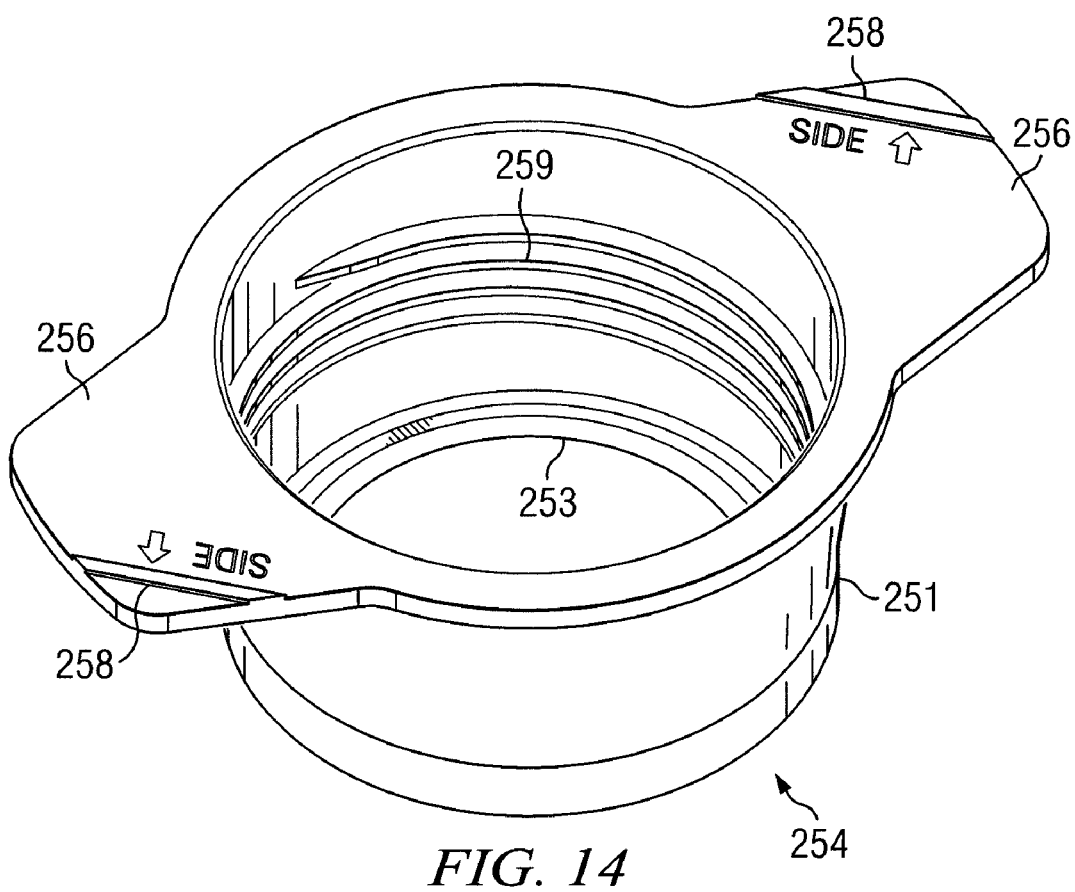
FIG. 14 illustrates a top perspective view of one embodiment of an insert sealing member.
Figure 15:
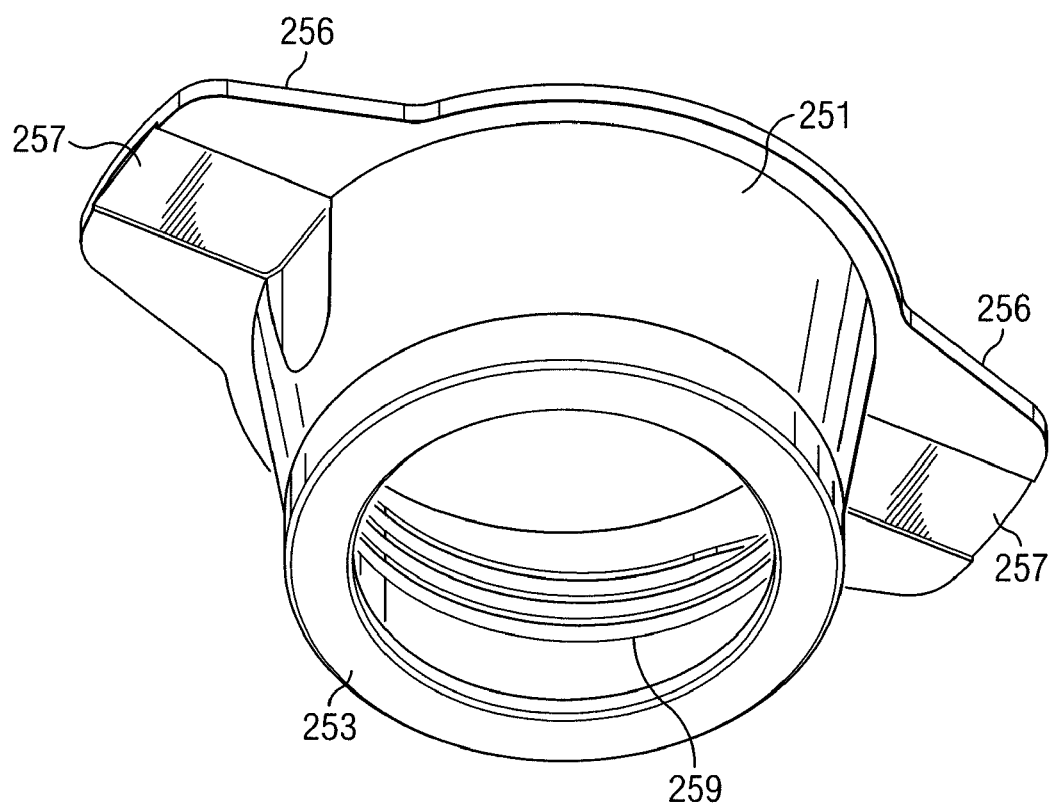
FIG. 15 illustrates a bottom perspective view of the embodiment of FIG. 14.
Figure 16:
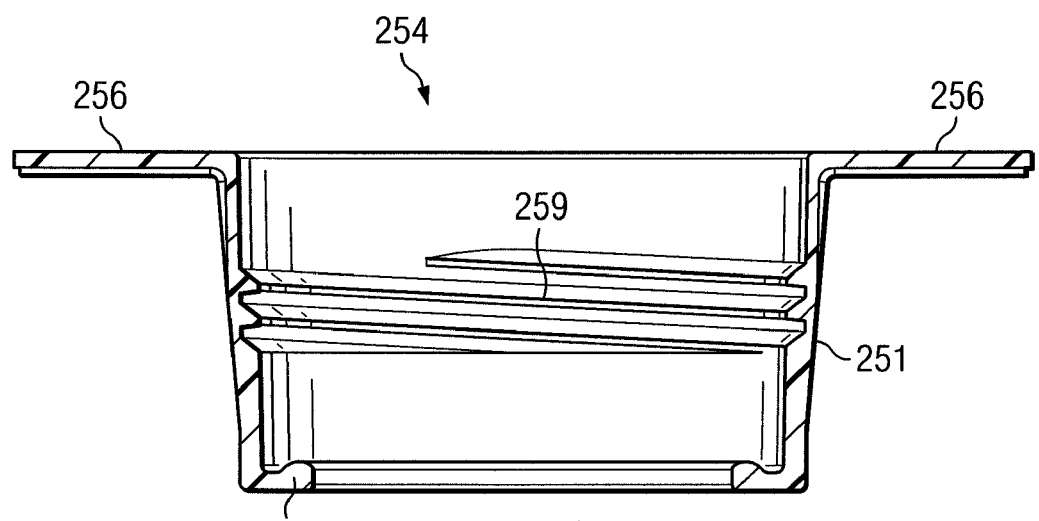
FIG. 16 illustrates a cross-sectional view of the embodiment of FIG. 14.

Referring now to FIGS. 14-16, more detailed features of insert sealing member 254 are visible. In this embodiment, insert sealing member 254 comprises a body 251 that is substantially cylindrical and has an internally threaded portion 259. In this embodiment, tabs 256 extend outwardly from one end of body 251, while lip 253 extends inwardly from the opposing end of body 251. Tabs 256 also comprise alignment indicia 258 and a pair of reliefs 257 to provide for clearance over sharp edge 300 (FIG. 2) of cell culture container 20.

Figure 17:
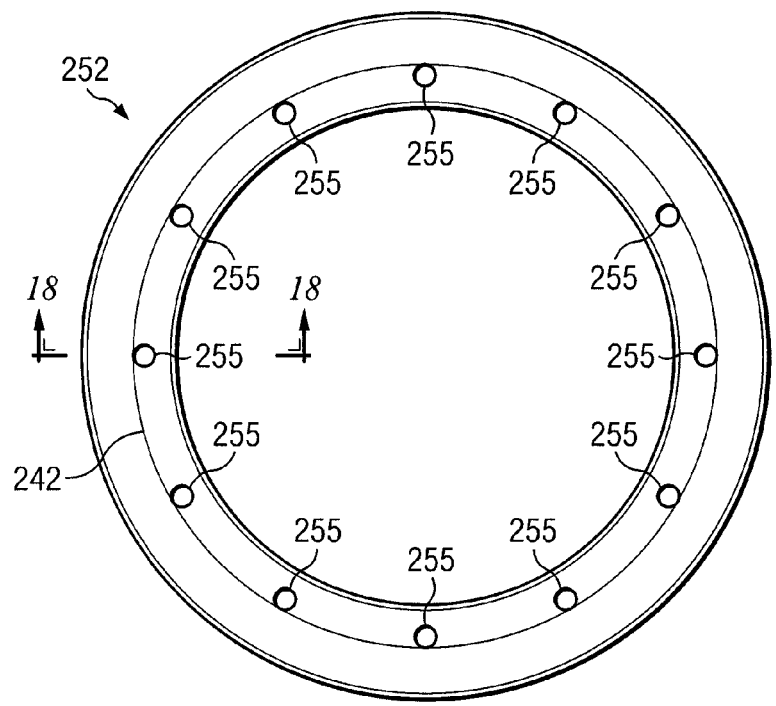
FIG. 17 illustrates a top view of one embodiment of an insert seal ring.
Figure 18:
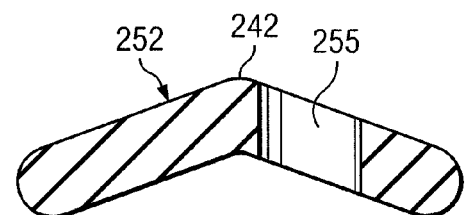
FIG. 18 illustrates a cross-sectional view of the embodiment of FIG. 17.

Referring now to FIGS. 17-18, more detailed features of insert seal ring 252 are visible. In this embodiment, insert seal ring 252 comprises a plurality of apertures 255. In addition, this embodiment of insert seal ring 252 comprises a ridge 242 so that the cross-section is slightly "V"-shaped, as shown in FIG. 18.

Figure 19:
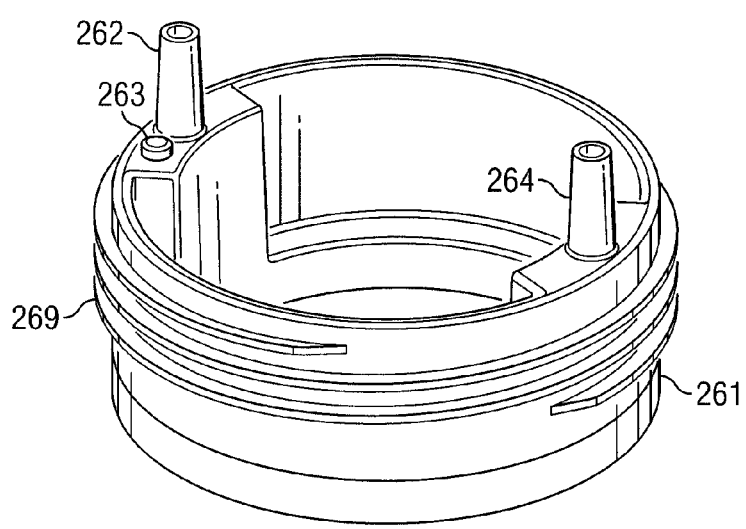
FIG. 19 illustrates a top perspective view of one embodiment of an insert manifold.
Figure 20:
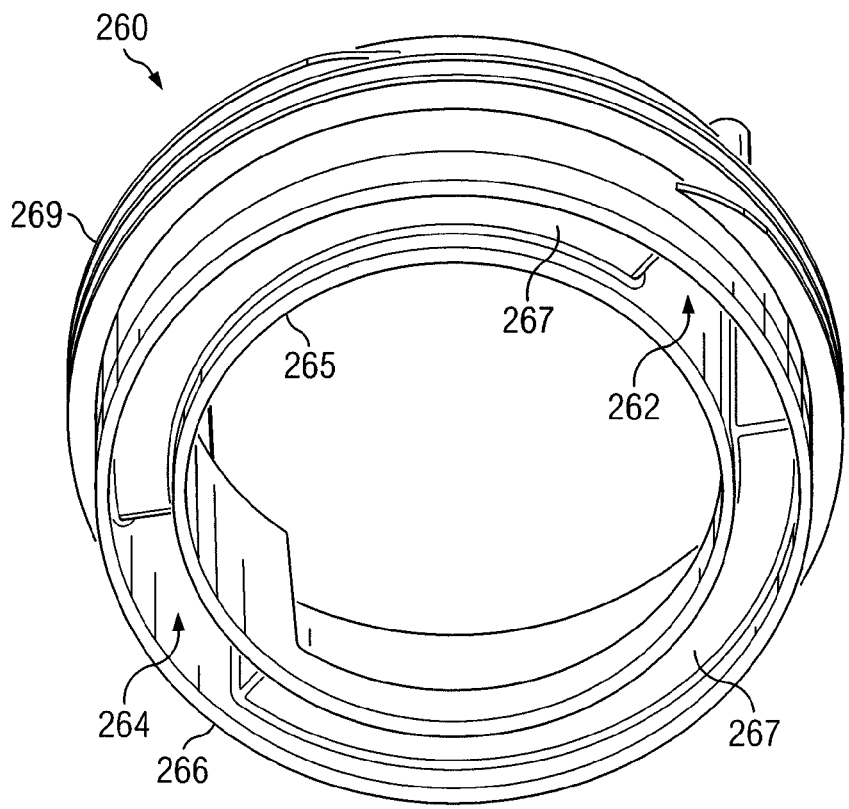
FIG. 20 illustrates a bottom perspective view of the embodiment of FIG. 19.
Figure 21:
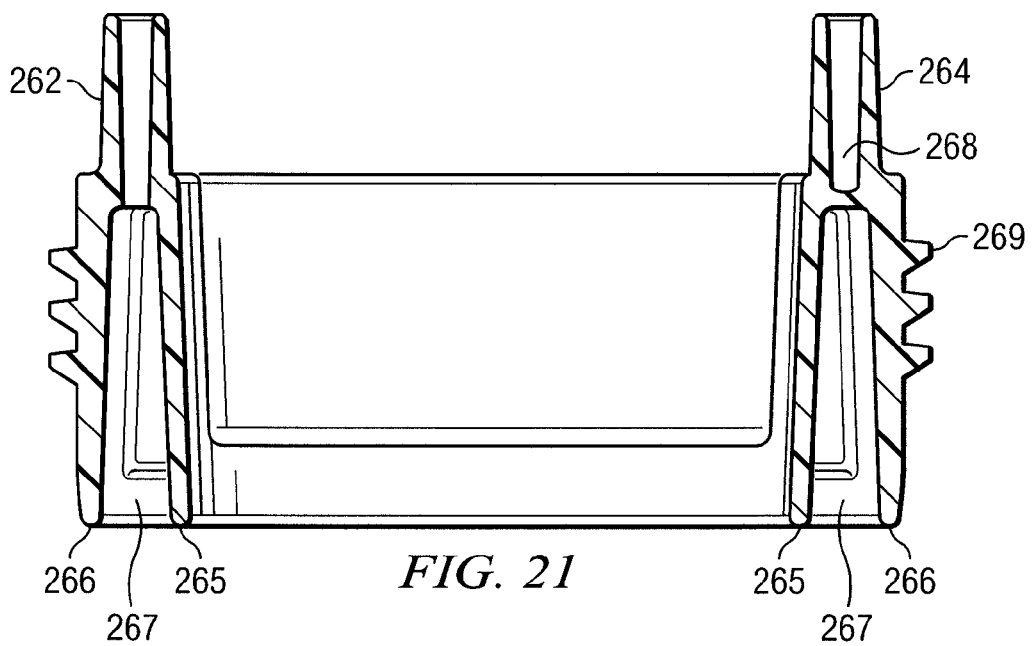
FIG. 21 illustrates a cross-sectional view of the embodiment of FIG. 20.

Referring now to FIGS. 19-21, more detailed features of insert manifold 260 are visible. In this embodiment, insert manifold 260 comprises a generally cylindrical body 261 with externally threaded portion 269. This embodiment also comprises a sealed conduit 264 that comprises a septum 268 that can be punctured if it is desired to open sealed conduit 264. If opened, sealed conduit 264 may be used for an additional low pressure conduit or for a pressure sensing port. In this embodiment, insert manifold 260 comprises a bump 263 that indicates that conduit 262 is open rather than sealed. Visible in FIGS. 20 and 21 are channel 267 (which is in fluid communication with conduit 262 and sealed conduit 264 if opened) and rounded edges 265 and 266. As shown in FIG. 9, rounded edges 265 and 266 may engage insert seal ring 252 such that channel 267 is in fluid communication with apertures 255 of insert seal ring 252.

Figure 22:
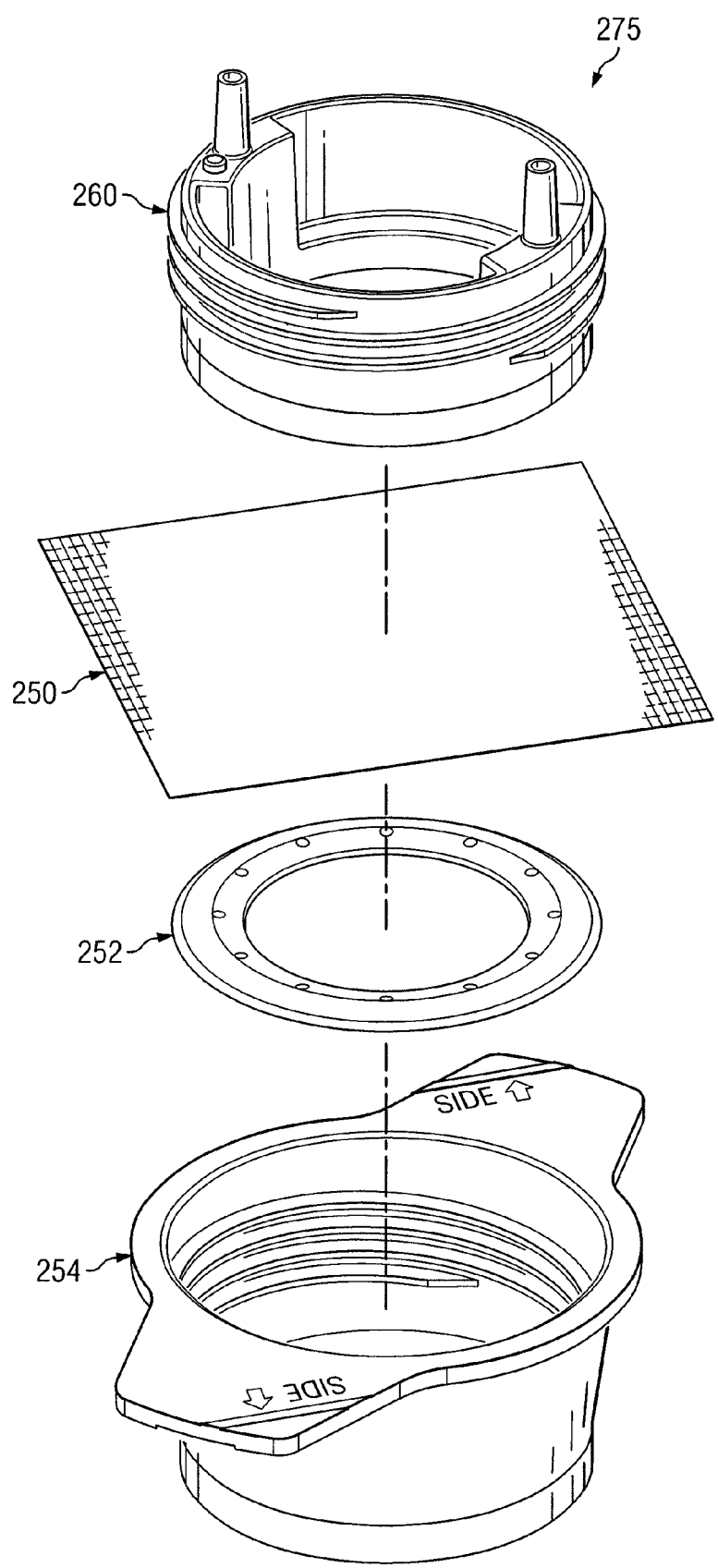
FIG. 22 illustrates an exploded view of one embodiment of an insert seal assembly.

Referring now to FIG. 22, insert manifold 260, drape 250, insert seal ring 252, and insert sealing member 254 are shown in an exploded view as one embodiment of an internal insert assembly 275. It is understood that in other embodiments, certain separate components of internal insert assembly 275 may be combined. For example, insert seal ring 252 may be integral to insert sealing member 254 or to insert manifold 260. During use, internal insert assembly 275 is configured to provide a seal across inner perimeter 29 of cell culture container 20. During assembly of the embodiment shown in FIG. 22, drape 250 is placed over insert seal ring 252, and excess material is trimmed from drape 250 around the perimeter of insert seal ring 252. Holes may then be created in drape 250 that are aligned with apertures 255 of insert seal ring 252. In the embodiment shown, insert manifold 260 may then be threaded into insert sealing member 254 such that rounded edges 275 and 266 engage drape 250 and compress it against insert seal ring 252 to form a substantially air tight seal with lip 253 of insert sealing member 254, as shown in FIG. 9. In addition, body 251 of insert sealing member 254 engages inner perimeter 29 of cell culture container 20, thereby creating a substantially air-tight seal across inner perimeter 29. As shown in the embodiment of FIG. 9, internal insert assembly 275 may therefore be combined with peripheral sealing member 230 to form a sealing system that provides substantially air-tight seals with inner perimeter 29 and exterior wall 19 of cell culture container 20. In the embodiment shown, tapered portion 239 of peripheral sealing member 230 engages exterior wall 19 in an interference fit and body 251 (near the interface with lip 253) engages inner perimeter 29 of cell culture container 20. Cell culture container 20 is therefore effectively sealed on both the exterior and interior, allowing for effective TNP to be applied to a cell matrix contained within cell culture container 20. In addition, cell culture system 200 may be combined with additional cell culture systems in a manner similar to that of cell culture system 100 shown in FIG. 6.

Figure 23:
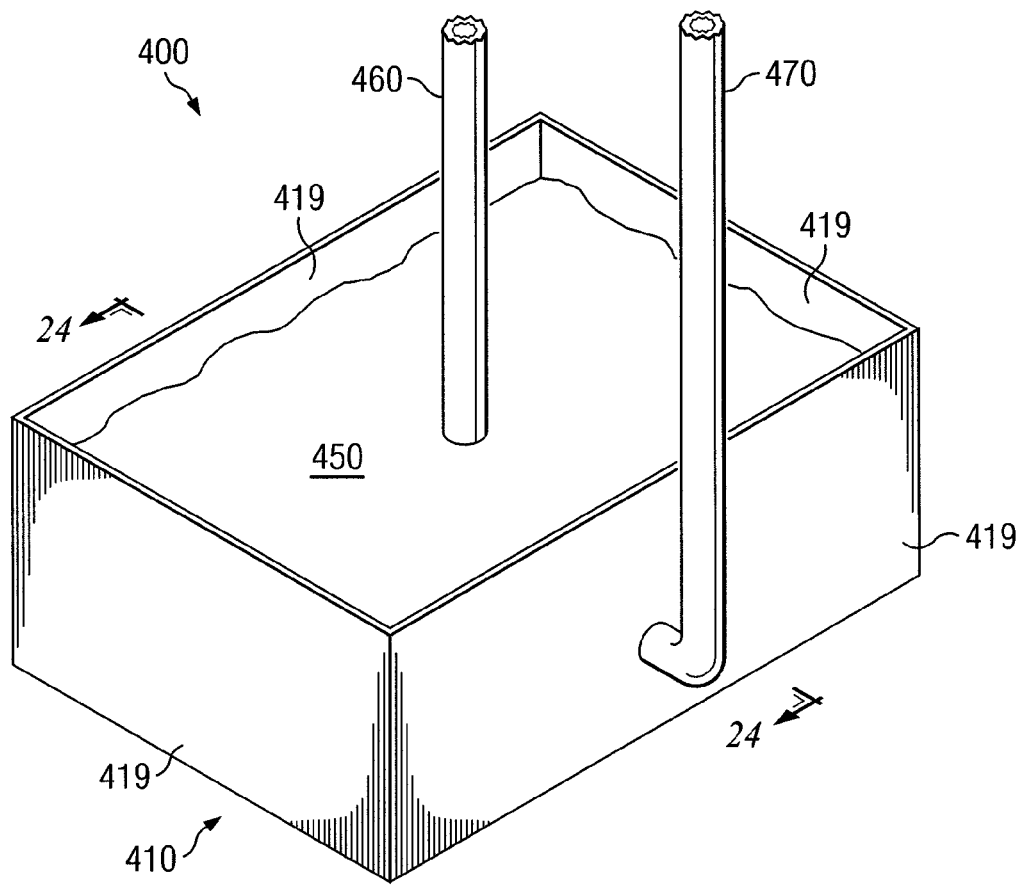
FIG. 23 illustrates a top perspective view of one embodiment of a cell culture system.
Figure 24:
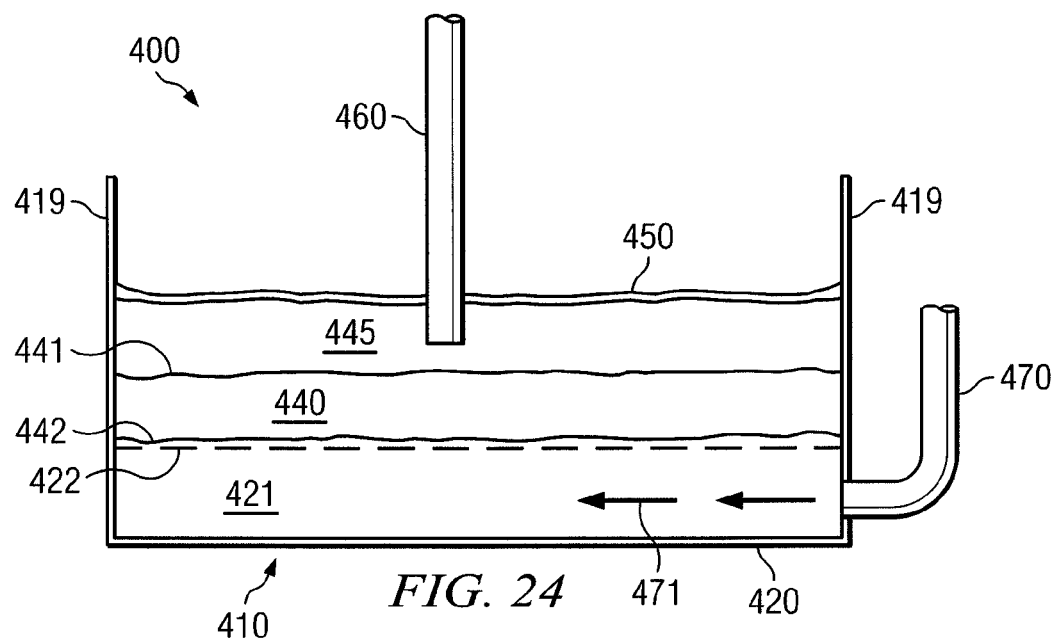
FIG. 24 illustrates a cross-sectional view of the embodiment of FIG. 23.

In other embodiments, the cell culture container may be any device suitable for culturing cells and may be a device other than a cell culture insert. Referring now to FIGS. 23 and 24, another embodiment of a cell culture system 400 is shown comprising a cell culture container 410 comprising peripheral walls 419 and floor 420. In this embodiment, cell culture container 410 comprises a cell culture matrix 440 between a permeable support 422 and a dressing 445. In the embodiment shown, a lid 450 covers dressing 445, and a suction conduit 460 (coupled to a low pressure source, not shown) may provide negative pressure to dressing 445 and cell culture matrix 440. In this embodiment, a culture media conduit 470 is coupled to cell culture container 410 and provides culture media 471, which can flow through permeable support 422 to cell culture matrix 440.

During use, this embodiment operates in a manner equivalent to the previously-described embodiments, and suction conduit 460 applies negative pressure to a first surface 441 (shown here as an upper surface) of cell matrix 440. In addition, culture media conduit 470 provides culture media 470 to a second surface 442 (shown here as a lower surface) of cell matrix 440. As shown, peripheral walls 419, floor 420, and lid 450 provide a substantially airtight enclosure 421 that effectively seals cell culture matrix 440 (with the exception of suction conduit 460 and culture media conduit 470). In this embodiment, suction conduit 460 extends through lid 450 and (when coupled to a low pressure source) can be used to control the amount of negative pressure that is applied to cell culture matrix 440. Similarly, culture media conduit 470 extends through peripheral wall 419 and can be used to control the amount of culture media 471 provided to cell culture matrix 440.

In the embodiment shown, cell culture container 410 does not require a separate peripheral sealing member between it and a larger assembly (such as a well plate) because cell culture media conduit 470 extends through peripheral wall 419 of cell culture container 410. Cell culture system 400 may operate with a single cell culture container 410 or multiple cell culture containers 410. In the embodiment shown, permeable support 422 may comprise any one of a number of different configurations. For example, permeable support 422 may comprise a mesh material, a perforated barrier, or membrane. In this embodiment, lid 450 may be a flexible drape similar to those in previously described embodiments, or lid 450 may be a more rigid member that engages peripheral walls 419 in a sealing manner. The disclosed embodiment is provided for purpose of example only, and modifications and variations of the disclosed embodiment are within the scope of the invention.

Throughout this disclosure, reference to a "seal between" two components does not require that the two components make contact with each other. Additional components may be located between two or more components that have a seal between them. Reference in this disclosure to "low", "reduced", "negative" or "suction" pressure refers to any pressure less than atmospheric pressure.

In certain embodiments, peripheral sealing member 230, insert sealing member 254 and insert manifold 260 (and other components) may be manufactured by injection molding. Other embodiments may comprise cast parts, non-standard o-ring sizes, or alternate materials. In certain embodiments, insert 20 and plate well 10 (as well as other components) may be standard components that are readily available (or "off-the-shelf") items. The utilization of such standard components can minimize the amount of sterilization that must be performed, because such components may be treated as disposable or consumable components.

In certain embodiments, the medium flow may be automatically controlled using a closed-loop feedback system that incorporates pressure, flow, or other parameter sensors, and the medium flow may be ramped, reversed, cycled or recycled. In certain embodiments, plate wells may be coupled in parallel or in series, and a gas injection or temperature control device may be added. In certain embodiments, optical radiation (UV to IR) may be added by incorporating LED's or other microelectronics to the system, as well as optical sensors or imaging devices. Electromagnetic, electrostatic, and magnetic fields may be induced by incorporating these field generators in or around the plate wells. Certain embodiments may comprise mechanical strain-inducing devices, such as MEMS, or microfluidics, and the system may be used for the study of nematodes, parasites, microbes, or small insects.

In certain embodiments, tissue samples having irregular shapes could be sealed to the insert by wax casting or similar means. In certain embodiments, portions of membrane 22 may be occluded and the apical surface of the culture may have a partially occluded cover in order to control the direction and velocity of the flow through the culture. For example, occluding all but the outer margin of membrane 22 and occluding all but a central hole in an apical cover could induce radial flow.

In certain embodiments, cell matrix 140 may comprise bovine fibrinogen and thrombin instead of plasma. Embodiments may also comprise various other biocompatible polymers and or extracellular matrix components such as Puramatrix™, chitosan, starch or collagen, provided cell matrix 140 is able to withstand TNP without collapsing. In other embodiments, cell matrix 140 may comprise resorbable materials, implantable mixes, tissue samples such as split thickness skin grafts or thin slices of tissue such as dentin or bone.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, in certain embodiments, peripheral sealing members 30 and 230 may be one component. In other embodiments, peripheral sealing members 30 and 230 may be comprised of multiple components.

In the foregoing Detailed Description of Disclosed Embodiments, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description of Disclosed Embodiments, with each claim standing on its own as a separate embodiment.

The invention claimed is:

1. A sealing system for applying a negative pressure to a cell matrix comprising:
 a cell container having sidewalls extending between an opening and a base, the base having a permeable portion for providing fluid communication with the cell matrix when positioned inside said cell container adjacent the base;
 a porous dressing for covering and fluidly communicating with the cell matrix when positioned within said cell container;
 a drape formed from a sheet of substantially gas-impermeable material extending to and sealing against the sidewalls for covering and sealing said porous dressing and the cell matrix within said cell container;
 a first conduit extending through said drape in fluid communication with said porous dressing for applying the negative pressure to the cell matrix through the porous dressing; and
 a well container having an open end covering and sealing the permeable portion of the base for applying a culture media to the cell matrix through the permeable portion of the base; and
 a lid adapted to cover the opening of said cell container.

2. The sealing system of claim 1, further comprising:
 a pump in fluid communication with said first conduit for delivering the negative pressure to said first conduit for supplying the negative pressure to said porous dressing for applying the negative pressure to the cell matrix.

3. The sealing system of claim 1, further comprising:
 a second conduit extending into said well container for supplying the culture media to the cell matrix.

4. The sealing system of claim 3, further comprising:
 a pump in fluid communication with said second conduit for delivering the cell media to said second conduit to supply the culture media to the cell matrix.

5. The sealing system of claim 3, wherein the drape is polyurethane.

6. The sealing system of claim 1, wherein porous dressing is an open-cell foam.

7. The sealing system of claim 1, wherein porous dressing is gauze.

8. The sealing system of claim 1, wherein the permeable portion of the base is a permeable membrane.

9. A sealing system for applying a negative pressure to a cell matrix comprising:
 a cell container having sidewalls extending between an opening and a base, the base having a permeable portion for providing fluid communication with the cell matrix when positioned inside said cell container adjacent the base;
 a porous dressing for covering and fluidly communicating with the cell matrix when positioned within said cell container;
 a drape formed from a sheet of substantially gas-impermeable material extending to and sealing against the sidewalls for covering and sealing said porous dressing and the cell matrix within said cell container;
 a first conduit extending through said drape in fluid communication with said porous dressing for applying the negative pressure to the cell matrix through the porous dressing;
 a sealing member having a substantially cylindrical body with an inside surface surrounding the sidewalls of said cell container and an outside surface adapted to seat within a plate well for applying a culture media to the cell matrix through the permeable portion of the base, a first seal disposed between the sidewalls and the inside surface of said sealing member, and a second seal disposed around the outside surface of said sealing member for providing a seal with the plate well to contain the culture media therein; and
 a lid adapted to cover the opening of said cell container.

10. The sealing system of claim 9, further comprising:
 a pump in fluid communication with said first conduit for delivering the negative pressure to said first conduit for supplying the negative pressure to said porous dressing for applying the negative pressure to the cell matrix.

11. The sealing system of claim 9, further comprising:
 a second conduit extending into well plate for supplying the culture media to the cell matrix.

12. The sealing system of claim 11, further comprising:
 a pump in fluid communication with said second conduit for delivering the cell media to said second conduit to supply the culture media to the cell matrix.

13. The sealing system of claim 9, further comprising:
 a second conduit extending through said sealing member into well plate for supplying the culture media to the cell matrix.

14. The sealing system of claim 9, further comprising:
 a second conduit extending through the second seal of said sealing member into well plate for supplying the culture media to the cell matrix.

15. The sealing system of claim 9, wherein the first seal is an O-ring.

16. The sealing system of claim 9, wherein the second seal is an O-ring.

17. The sealing system of claim 9, wherein the drape is polyurethane.

18. The sealing system of claim 9, wherein porous dressing is an open-cell foam.

19. The sealing system of claim 9, wherein porous dressing is gauze.

20. The sealing system of claim 9, wherein the permeable portion of the base is a permeable membrane.

* * * * *

UNITED STATES PATENT AND TRADEMARK OFFICE
CERTIFICATE OF CORRECTION

| | | |
|---|---|---|
| PATENT NO. | : 7,981,668 B2 | Page 1 of 1 |
| APPLICATION NO. | : 11/624017 | |
| DATED | : July 19, 2011 | |
| INVENTOR(S) | : Robert P. Wilkes et al. | |

It is certified that error appears in the above-identified patent and that said Letters Patent is hereby corrected as shown below:

Col. 11, line 46
The dependency of claim 5 should be changed from "claim 3" to --claim 1--.

Signed and Sealed this

Eighteenth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,981,668 B2 | Page 1 of 1 |
| APPLICATION NO. | : 11/624017 | |
| DATED | : July 19, 2011 | |
| INVENTOR(S) | : Robert P. Wilkes et al. | |

It is certified that error appears in the above-identified patent and that said Letters Patent is hereby corrected as shown below:

Col. 11 line 44 the term "cell media" listed in claim 4 should be corrected to read --culture media--.

Col. 12 line 35 the term "cell media" listed in claim 12 should be corrected to read --culture media--.

Signed and Sealed this
Eighth Day of November, 2011

David J. Kappos
*Director of the United States Patent and Trademark Office*